United States Patent [19]

Pomerantzeff

[11] 4,357,088
[45] Nov. 2, 1982

[54] MACULA-DISC CAMERA WITH IMPROVED RESOLUTION

[75] Inventor: Oleg Pomerantzeff, Brookline, Mass.

[73] Assignee: The United States of America as represented by the Department of Health and Human Services, Washington, D.C.

[21] Appl. No.: 239,448

[22] Filed: Mar. 2, 1981

[51] Int. Cl.³ .............................................. A61B 3/14
[52] U.S. Cl. ........................................ 354/62; 351/7; 351/16
[58] Field of Search .................... 354/62; 351/6, 7, 16

[56] References Cited

U.S. PATENT DOCUMENTS

| | | | |
|---|---|---|---|
| 3,770,342 | 11/1973 | Dudragne | 351/6 X |
| 3,780,979 | 12/1973 | de Guillebon | 351/16 |
| 3,944,341 | 3/1976 | Pomerantzeff | 354/62 X |
| 4,023,189 | 5/1977 | Govignon | 354/62 |
| 4,056,310 | 11/1977 | Shimizu et al. | 351/16 X |
| 4,265,519 | 5/1981 | Pomerantzeff | 351/16 |

*Primary Examiner*—John Gonzales
*Attorney, Agent, or Firm*—Holman & Stern

[57] ABSTRACT

A macula-disc camera records the first aerial image of the patient's fundus to provide an actual increase in resolution of retinal detail not obtainable by merely magnifying this image with the recording optics. An array of optical fibers surrounds the contact lens to illuminate a limied field of the fundus, on the order of 18°. A high degree of contrast is achieved by tightly separating the observation and illumination beams throughout the lens of the cornea and crystalline lens. Magnification, is on the order of 6.8 times.

13 Claims, 4 Drawing Figures

MACULA-DISC CAMERA WITH IMPROVED RESOLUTION

TECHNICAL FIELD

The present invention relates to ophthalmoscopic cameras in general and, more particularly, to a macula-disc camera having improved resolution.

BACKGROUND OF THE INVENTION

In order to increase the resolution of retinal detail in fundus cameras it is necessary to increase the magnification and thereby clarify microscopic details. In the prior art, greater magnification has been realized only by increasing the magnification of the recording camera, thereby magnifying one part of the intermediate aerial image without changing the objective (i.e. ophthalmoscopic lens) of the fundus camera. The only retinal information that the fundus camera can provide is contained in the aerial image formed by the ophthalmoscopic lens. Therefore, magnifying this image with the use of the recording optics instead of enlarging the negative only results in blowing up the image without simultaneously magnifying the grain of the film. On the other hand, magnifying the first image formed by the ophthalmoscopic lens increases the information from the fundus itself. One way to accomplish magnification of the first image formed by the ophthalmoscopic lens is to reduce the dioptric power of that lens. The improvement gained by this means, however, is limited. The ophthalmoscopic lens is used not only for imaging the retina but also for imaging the light source and the recording camera stop onto the patient's pupil. Reducing the power of this lens, therefore, results in an increase in the size of these images in the pupil, rendering their separation more difficult. Contrast, especially in fluorescein angiography, depends primarily upon maximizing the avoidance of stray light in the path of observation. It is therefore of crucial importance, if increased resolution is to be obtained, to maintain separation of the observation and illumination beams.

SUMMARY OF THE INVENTION

It is therefore an object of the present invention to provide a fundus camera having improved resolution of the retinal image over that permitted by prior art cameras. It is another object of the present invention to provide a small-field, high magnification fundus camera having improved resolution.

In accordance with the present invention there is provided a macula-disc camera, which is a contact camera, having no intermediate image. The contact system provides excellent separation of the illumination and observation beams in the cornea and crystalline lens. The contact arrangement also has the advantage of reducing the optical system to a small number of surfaces and permits a considerably larger entrance pupil for the light collected from the fundus. A stop is provided at the contact surface of the contact lens in order to limit the apertures of bundles in the pupillary plane and thereby increase the quality of the aerial image. Further, the contact system, by replacing the air-cornea interface with a contact lens, reduces the effect of assymmetry of the cornea to a negligible level.

BRIEF DESCRIPTION OF THE DRAWINGS

The above and still further objects, features and advantages of the present invention will become apparent upon consideration of the following detailed description of the embodiments thereof, especially when taken in conjunction with the accompanying drawings, wherein.

DESCRIPTION OF THE PREFERRED EMBODIMENTS

Figure 1:
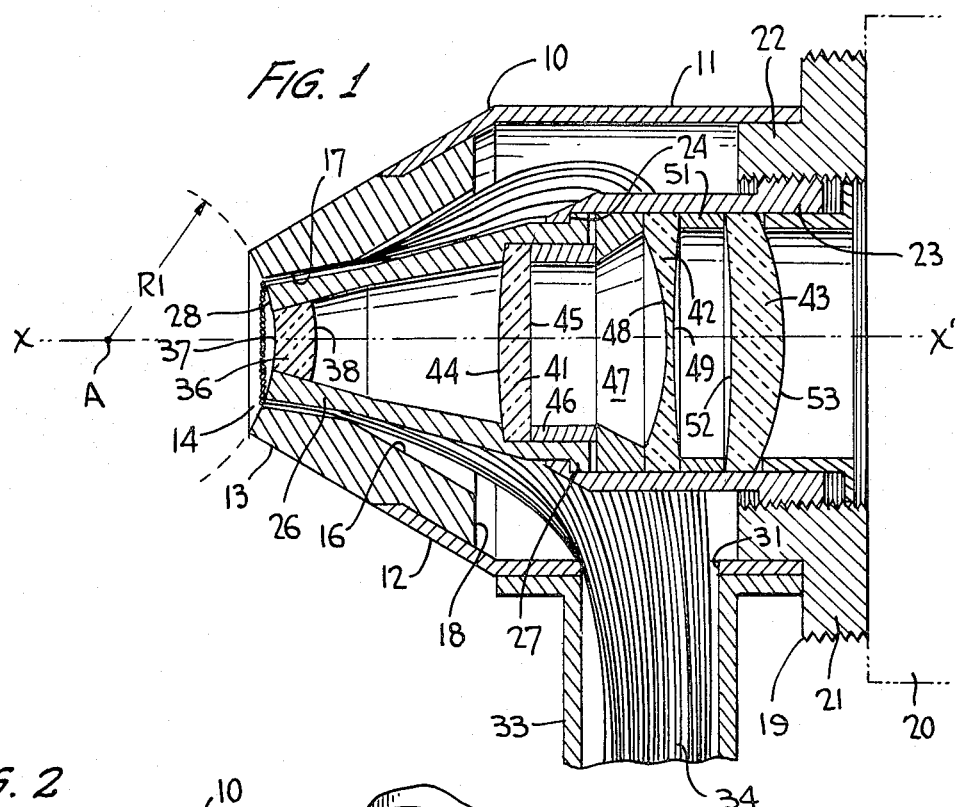
FIG. 1 is a cross-sectional view of a fundus camera constructed in accordance with the present invention.
Figure 2:
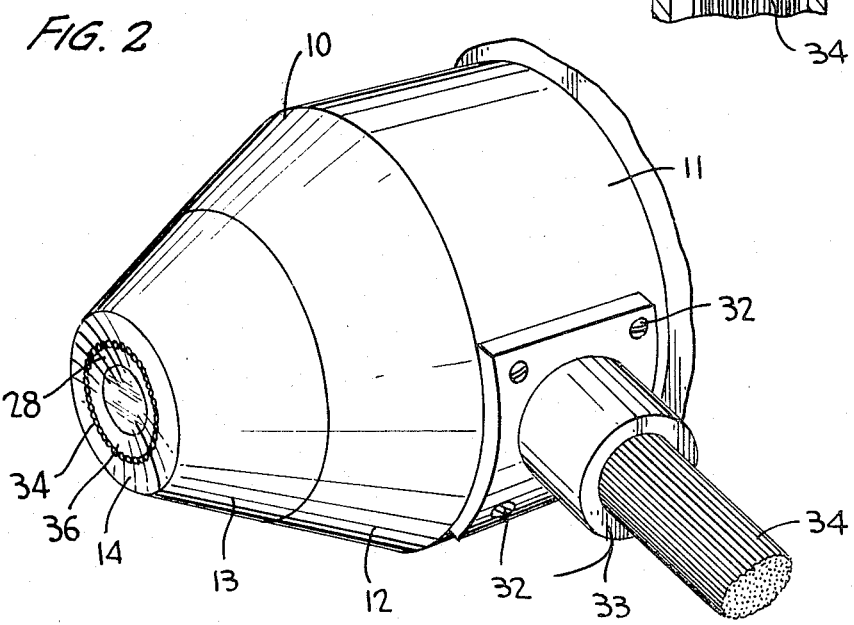
FIG. 2 is a view in perspective of the camera of FIG. 1.

Referring specifically to FIGS. 1 and 2 of the accompanying drawings, an outer housing 10 includes a rearward hollow cylindrical section 11 and a forward frusto-conical section 12. An outer cone 13 of generally frusto-conical configuration is fitted into and secured to the forward section 12 of housing 10. More particularly, a rearward portion of the peripheral wall of cone 13 is cut away (i.e. of reduced diameter) in the configuration corresponding to the forward section 12 of housing 10. In this manner, the forward portion of the periphery of cone 13 externally appears as a smooth extension of housing section 12. The hollow interior of cone 13 is bounded by a surface having a rear section 16 and a forward section 17. Surface 16 is substantially parallel to the exterior surface of cone 13. Forward surface 17, which bends abruptly away from surface 16, forms a much smaller angle with the central longitudinal axis of cone 13 than does surface 16. The rearward facing end 18 of cone 13 is in the form of an annulus. The forward facing end 14 of cone 13 is in the form of an annular segment of a sphere having a radius R1, the sphere being centered about a point A disposed forwardly of forward end 14 of cone 13. Cone 13 is secured to section 12 of housing 10 by means of any suitable adhesive material.

A lens base 19 is threadedly engaged by a camera 20, the latter being shown in phantom. Lens base 19 is in the form of a hollow top hat wherein its exterior includes a widened cylindrical section 21 at its forward end and a narrower (i.e. lesser diameter) cylindrical section at its forward end. The surface defining the hollow interior of lens base 19 is of constant diameter throughout its length and is threaded for purposes described below. The exterior surface of section 21 of lens base 19 is threaded to permit engagement with camera 20. The diameter of the outer wall of section 22 of lens base 19 is substantially equal to, or very slightly smaller than, the diameter of the interior surface of section 11 of housing 10, whereby lens base section 22 fits concentrically into the end portion of housing section 11 with lens base section 21 serving as a stop for the extent of insertion. A suitable adhesive material is utilized to secure lens base to housing section 11.

A hollow lens housing member 23 has its exterior subdivided into three sections, namely: a rearward section, of greater diameter than the other two, which is externally threaded to engage the internal threads of lens base 19; a middle section of cylindrical configuration which is considerably longer than the other two sections; and a forward section of generally frusto-conical configuration and converging toward the longitudinal axis of the member in the forward direction. The interior surface of lens housing 23 is subdivided into two sections, namely: a small cylindrical rearward section extending throughout most of the length of the lens housing; and a short cylindrical forward section separated from rearward section by an annular rearward-facing shoulder 24 disposed longitudinally even with the converging forward end of the outer surface.

An inner lens cone 26 has at its rearward end an annular flange 27 which projects radially outward to engage shoulder 24 of the lens housing 23 when the inner lens cone 26 is coaxially inserted with its forward end first through the rear of lens housing 23. By means of suitable adhesive material, flange 27 is secured to the interior of the lens housing proximate shoulder 24. Forwardly of the lens housing 23, inner lens cone 26 tapers in a conical manner to extend coaxially within outer cone member 13 while providing a hollow conical space between it and the rearward section 16 of member 13. The portion of the inner lens cone 26 which extends within forward section 17 of outer cone 13 is parallel to section 17, defining a frusto-conical space therebetween having a cross-section, viewed transversely to the longitudinal axis, which is annular. The forward end 28 of hollow inner lens cone 26 is an annular segment of a sphere having a radius R1 and centered about point A. Thus, forward end 14 of outer cone 13 and forward end 28 of inner cone 26 reside on the same spherical surface.

Cylindrical section 11 of housing 10 is provided with an aperture 31 over which is secured, by means of screws 32, or the like, a support mount 33 for a bundle 34 of optical fibers. The optical fibers transmit light from an illuminator source (not shown) in a conventional manner. The optical fibers 34 extend through the support mount 33 into the generally annular space between housing section 11 and lens housing 23 from which point the fibers are oriented into the space between outer conical member 13 and inner conical member 26. More specifically, the optical fibers 34 are disposed in a circular pattern in the space between forward section 17 of conical member 13 and the forward section of the exterior surface of inner cone 26. For purposes of reference, in this regard, the optical fibers are arranged in a single ring similar to that described and illustrated in my prior U.S. Pat. No. 3,944,341, the subject matter of which is incorporated herein for purposes of reference. The optical fibers terminate in the surface of the unit defined by end sections 14 and 28 of the outer and inner cones, respectively.

A contact lens 36 is secured, by means of suitable adhesive material or the like, in the interior of inner lens cone 26 and at the forward end thereof. The forward facing surface of contact lens 36 is a segment of a sphere having radius R1 and centered about point A. Therefore, the forward ends 14 and 28 of conical members 13 and 26, respectively, along with the forward ends of the optical fibers 34 and the forward surface of lens 36 form a common segment of a sphere having radius R1 and centered about point A. Contact lens 36 is preferably formed of a glass sold by the Eastman Kodak Company of Rochester, New York under their designation EK-911. This glass has a refractive index of 2.1. Another glass suitable for use as contact lens 36 is sold by Jenaer Glaswerk Schott & Gen. Mainz, West Germany under their designation LaSF 6-961349. This latter glass has a reflective index of 1.96052. The radius of curvature R1 of the forward surface 37 of lens 36 is 8.2 mm. The rear surface 38 of lens 36, which is convex facing rearward, has a radius of curvature of 10.4 mm. The thickness of lens 36 along the longitudinal axis X—X' of the device is 2.0 mm.

A series of lenses 41, 42 and 43 are spaced longitudinally along axis X—X', rearwardly of contact lens 36. Lens 41 is a double convex lens secured interiorly of inner core 26 in a suitably provided rearward facing annular shoulder. The forward surface 44 of lens 41 is spaced 9.0 mm from the rearward surface 38 of lens 36. This spacing, as with all lens spacings described herein, is along the axis X—X'. Convex forward surface 44 of lens 41 has a radius of curvature of 32.05 mm. The rearward, slightly convex surface 45 of lens 41 has a radius of curvature of 265.25 mm. The thickness of lens 41, again along axis X—X', is 1.55 mm. An annular spacer 46 has its forward annular edge abutting the radially outward periphery of surface 45 of lens 41 and serves as a longitudinal spacer between lens 41 and an aperture element 47. Aperture element 47 is disposed concentrically about axis X—X' and has a cylindrical outer wall and a frusto-conical inner wall which tapers in a forward direction. The forward edge of the inner wall of aperture element 47 determines the optical aperture for lenses 42 and 43.

Lens 42 is a double concave lens positioned with the radially outward portion of its forward end abutting aperture element 47. The forward facing concave surface 48 of lens 42 has a radius of curvature of 14.783 mm and is spaced, on axis, from the rear surface 45 of lens 41 by a distance of 6.6 mm. The rearward concave surface 49 of lens 42 has a radius of curvature of 60.289 mm. The thickness of lens 42, on axis, is 0.7 mm.

A further annular spacer is positioned between lens 42 and lens 43. The forward concave surface 52 of lens 43 has a radius of curvature of 160.6 mm and is spaced, on axis, from the rearward surface 49 of lens 42 by a distance of 2.41 mm. The rearward convex surface 53 of lens 43 has a radius of curvature of 14.783 mm. The thickness of lens 43, on axes, is 2.97 mm.

Figure 3:
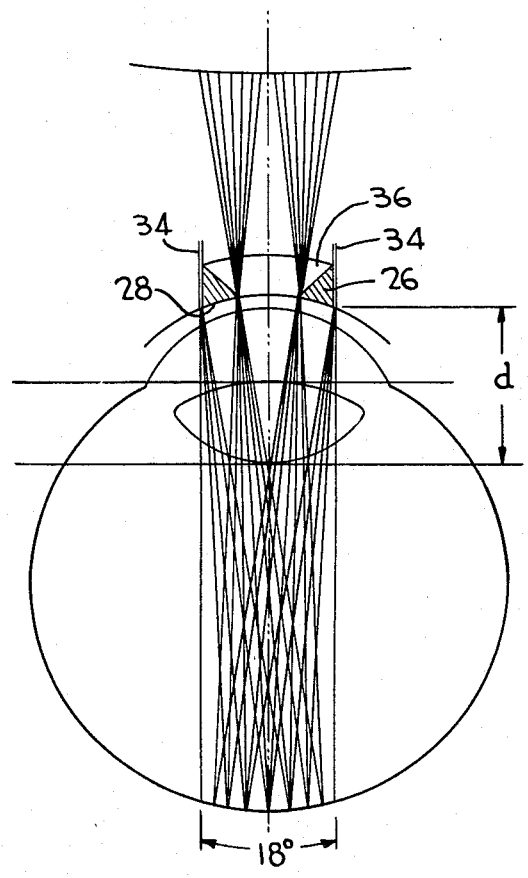
FIG. 3 is a light ray diagram of the illumination and observation bundles in reference to an eye being photographed.

Referring to FIG. 3, a computer ray plot through the ocular media and contact lens 36 is illustrated. As previously noted, contrast, especially in angiography, depends primarily upon maximal avoidance of stray light in the path of observation. This is achieved by tightly separating the observation beam (through lens 36) and the illumination beam (from optical fibers 34). As clearly seen in FIG. 3, these beams are completely separated throughout the region d of the cornea and crystalline lens of the patient's eye. The improvement in resolution provided by the present invention is obtained by increasing the magnification of the first retinal image formed by the opthalmoscopic lens in air. The diameter of the field is 18° and represents an arc of approximately 5.4 mm on the retina. This field is magnified 6.8 times so that its diameter in the retinal image is 5.4×6.8 or 36.72 mm. The frame of the camera cuts out a rectangular image measuring 35 mm by 24 mm in this aerial image. Therefore the real retinal field on the film is 35/6.8=5.15 mm, or 17.21°, along the long side of the frame. The entire field of 18° is represented along the diagonal of the frame, and a field of approximately 12° along its short side.

As noted above, the use of a contact arrangement provides for excellent separation of the illumination and observation beams in the cornea and crystalline lens. In addition, this arrangement has the advantage of reducing the optical system to a small number of surfaces. Further, the system permits a considerably larger entrance pupil for the light collected from the fundus.

Only one disadvantage of the contact system is that there is no limiting stop as to the contact lens and therefore no way of limiting the apertures of bundles in the pupillary plane. The rims of the lenses that follow the contact lens can not be considered as stops since they would accept, for any retinal point, all of the rays filling the widely dilated pupil. It is known that, without stopping the bundles in the pupil, the aerial image is of poor quality. For these reasons, a stop is built into the contact lens in the form of the interior edge of end surface 28 of inner core 26. This edge defines an aperture of 3 mm in diameter at the contact surface. This arrangement considerably opens the apertures of the image-forming bundles, i.e., their individual entrance pupils. The collecting aperture in this camera is on the order of 4.5 times wider than the same aperture in prior art cameras. This larger collecting pupil permits an increase in the number of frame per second and reduces the level of illuminating blue light.

Figure 4:
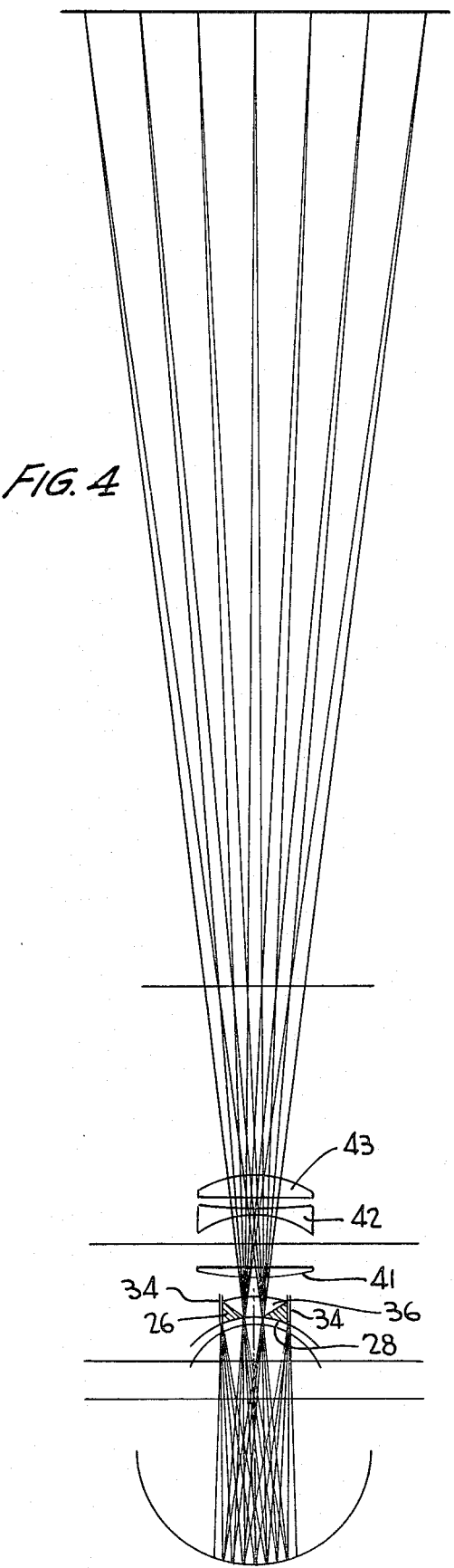
FIG. 4 is a complete sketch of the light rays in the camera of the present invention.

The computer ray tracing of FIG. 4 is an expansion of that of FIG. 3 in that it illustrates the entire macular camera. The geometric resolution in the image is less than 20 μm throughout the field. With a magnification of 6.8, this represents a geometrical resolution of about 3 μm in the retina, assuming a contrast of 1. Although the real contrast in the fundus is far from that, the contrast in fluorescein angiography is close to 1 when well-matched filters and well-separated collecting and illuminating pupils are utilized. Therefore, small capillaries can be resolved with the camera of the present invention.

The invention described hereinabove is a small-field high-magnification macula-disc camera which is a contact camera having no intermediate image. The field of view is 18° (from the nodal point) and the magnification, limited by a 35 mm film, is 6.8 times. By eliminating the intermediate image and magnifying instead the first aerial image, resolution is increased well beyond that achievable in the prior art.

The invention may be embodied in other specific forms without departing from the spirit or essential characteristics thereof. The disclosed preferred embodiment is therefore to be considered in all respects as illustrative and not restrictive, the scope of the invention being indicated by the appended claims rather than by the foregoing description, and all changes which come within the meaning and range of equivalency of the claims are therefore intended to be embraced therein.

I claim:

1. Optical image forming apparatus for use with a fundus camera having an optical axis, said apparatus comprising:
an inner hollow generally conical member having a forward end;
an outer hollow generally conical member having a forward end and disposed concentrically about and spaced from said inner member;
a contact lens disposed radially interiorly of said inner member, at the forward end of said inner member, through which the interior of an eye can be photographed; and
an array of optical fibers disposed in the space between said inner and outer members, surrounding said contact lens, for illuminating a field of approximately 18° of the fundus of the eye to be photographed; wherein said contact lens is positioned to provide an optical image of the illuminated portion of said fundus.

2. The apparatus according to claim 1 further comprising a plurality of lenses spaced along said optical axis for magnifying the image provided by said contact lens.

3. The apparatus according to claim 2, wherein the total magnification of the image of the illuminated portion of said fundus provided by said contact lens and said series of lenses is on the order of 6.8 times.

4. The apparatus according to claims 1, 2 or 3 further comprising means for defining an optical aperture on the order of 3 mm for said contact lens.

5. The apparatus according to claim 4, wherein said means for defining an optical aperture comprises a forward interior annular edge of said inner member.

6. The apparatus according to claims 1 or 2, wherein said contact lens has a forward concave surface having a radius of curvature of 8.2 mm, a rear convex surface having a radius of curvature of 10.4 mm, and a thickness between said forward and rear surfaces along said optical axis of 2 mm.

7. The apparatus according to claim 6, wherein said series of lenses includes a second lens, a third lens and a fourth lens sequentially,
wherein said second lens has a forward convex surface having a radius of curvature of 32.05 mm which is spaced along said optical axis at distance of 9 mm from said rear surface of said contact lens, said second lens having a rear concave surface with a radius of curvature of 265.25 mm, wherein the thickness of said second lens along said optical axis is 1.55 mm;
wherein said third lens has a forward concave surface with a radius of curvature of 14.783 mm spaced along said optical axis a distance of 6.6 mm from the rear surface of said second lens, said third lens including a rear concave surface having a radius of curvature of 60.289 mm, wherein the thickness of said third lens along said optical axis is 0.7 mm; and
wherein said fourth lens has a forward concave surface having a radius of curvature of 160.6 mm and spaced along said optical axis a distance of 2.41 mm from said rear surface of said third ens, said fourth lens having a rear convex surface with a radius of curvature of 14.783 mm, the thickness of said fourth lens along said optical axis being 2.97 mm.

8. The apparatus according to claim 7, further comprising aperture-defining means disposed along said optical axis between said second and third lenses.

9. The apparatus according to claim 1, further comprising means for completely separating, throughout the cornea and crystalline lens of an eye being photographed, light beams emitted from said optical fibers and image-forming beams reflected from the illuminated portion of the fundus of the eye being photographed.

10. Optical image forming apparatus for use with a fundus camera having an optical axis, said apparatus comprising:
an inner hollow generally conical member having a forward end;
an outer hollow generally conical member having a forward end and disposed concentrically about and spaced from said inner member;
a contact lens disposed interiorly of said inner member, at the forward end of said inner member, through which the interior of an eye can be photographed;

an array of optical filters disposed in a space between said inner and outer members surrounding said contact lens for illuminating a relatively small field of the fundus of the eye to be photographed; and means for tightly separating, throughout the lens of the cornea and crystalline lens of the eye being photographed, the illuminating beam emanating from said optical fibers and the reflected image of the illuminated portion of the fundus.

11. The apparatus according to claim 10, further comprising a plurality of lenses spaced along said optical axis for magnifying the image provided by said contact lens.

12. The apparatus according to claim 11, wherein said series of lenses includes a second lens, a third lens and a fourth lens sequentially, wherein said second lens has a forward convex surface having a radius of curvature of 32.05 mm which is spaced along said optical axis at a distance of 9 mm from said rear surface of said contact lens, said second lens having a rear concave surface with a radius of curvature of 265.25 mm, wherein the thickness of said second lens along said optical axis is 1.55 mm;

wherein said third lens has a forward concave surface with a radius of curvature of 14.783 mm spaced along said optical axis a distance of 6.6 mm from the rear surface of said second lens, said third lens including a rear concave surface having a radius of curvature of 60.289 mm, wherein the thickness of said third lens along said optical axis is 0.7 mm; and wherein said fourth lens has a forward concave surface having a radius of curvature of 160.6 mm and spaced along said optical axis a distance of 2.41 mm from said rear surface of said rear lens, said fourth lens having a rear convex surface with a radius of curvature of 14.783 mm, the thickness of said fourth lens along said optical axis being 2.97 mm.

13. The apparatus according to claim 11, wherein the total magnification of the image of the illuminated portion of said fundus provided by said contact lens and said series of lenses is on the order of 6.8 times.

* * * * *